United States Patent [19]

Fuss et al.

[11] Patent Number: 4,924,014

[45] Date of Patent: May 8, 1990

[54] PROCESS FOR THE PREPARATION OF HALOGEN-CONTAINING AROMATIC COMPOUNDS

[75] Inventors: Andreas Fuss, Karlstein; Günter Siegemund, Hofheim am Taunus, both of Fed. Rep. of Germany

[73] Assignee: Hoechst Aktiengesellschaft, Frankfurt am Main, Fed. Rep. of Germany

[21] Appl. No.: 316,794

[22] Filed: Feb. 28, 1989

[30] Foreign Application Priority Data

Mar. 2, 1988 [DE] Fed. Rep. of Germany ....... 3806656

[51] Int. Cl.$^5$ ............................................. C07C 45/46
[52] U.S. Cl. ...................................... 568/323; 568/34
[58] Field of Search ................. 568/34, 319, 322, 323

[56] References Cited

U.S. PATENT DOCUMENTS

| | | | |
|---|---|---|---|
| 4,454,350 | 6/1984 | Desbois | 568/323 |
| 4,554,381 | 11/1985 | Desbois | 568/34 |
| 4,618,726 | 10/1986 | Desbois | 568/323 |

FOREIGN PATENT DOCUMENTS

| | | | |
|---|---|---|---|
| 0084742 | 8/1983 | European Pat. Off. | 568/319 |
| 0199661 | 10/1986 | European Pat. Off. | 568/319 |
| 3531837 | 3/1987 | Fed. Rep. of Germany | 568/319 |
| 54-135756 | 10/1979 | Japan | 568/323 |
| 60-188343 | 9/1985 | Japan | 568/323 |
| 1139296 | 1/1969 | United Kingdom | 568/319 |

OTHER PUBLICATIONS

P. M. Hergenrother et al., *J. Polymer Sci.,* Part A, Polymer Chemistry, 25, 1094-1103 (1987).

*Primary Examiner*—James H. Reamer

[57] ABSTRACT

A process for the preparation of halogen-containing aromatic compounds of the formula I

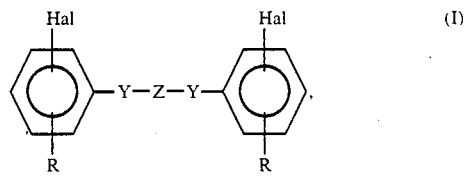

wherein
Hal represents halogen,
R represents H, $C_1$-$C_3$-alkyl, phenyl, halogen or trifluoromethyl,
Y represents CO or $SO_2$ and
Z represents an aromatic or heteroaromatic group, and
Y-Z-Y together may also be CO or $SO_2$, which comprises reacting a haloaromatic compound of the formula $RC_6H_4Hal$ (II) with a halide of a bisacid having the formula Hal-Y-Z-Y-Hal (III) in a molar ratio of at least 2:1 in the presence of hydrogen fluoride and or boron trifluoride, in formulae II and III Hal, R, Y and Z having the aforementioned meaning.

26 Claims, No Drawings

PROCESS FOR THE PREPARATION OF HALOGEN-CONTAINING AROMATIC COMPOUNDS

DESCRIPTION:

The invention relates to a process for the preparation of halogen-containing aromatic compounds which contain at least two aromatic rings which are bonded to one another via at least one bridging member.

The preparation of 1,4-bis-(4-chlorobenzoyl)-benzene is disclosed in GB Pat. 1,139,296, where 700 parts (6.22 mol) of chlorobenzene are reacted at 130° C. in the course of 6 hours with 97 parts (0.48 mol) of terephthaloyl dichloride and 145 parts (1.09 mol) of powdered anhydrous aluminum chloride. A yield is not reported. The analogous reaction of fluorobenzene is described, inter alia, in DE-A-3,531,837, the halobenzene (in this case fluorobenzene), aluminum chloride and terephthaloyl dichloride being used in virtually the same molar ratios as in GB Pat. 1,139,296. However, the yield reported for 1,4-bis-(4-fluorobenzoyl)-benzene in DE-A-3,531,837 is dubious since more product is obtained after purification (1250 g) than was present as crude product (1225 g). Also, the melting incorrectly reported as 121° C. (instead of 218.5° to 219.5° C. according to Hergenrother et al. in Journ. Pol. Sci., part A, Polymer Chemistry, 25, 1094 (1987)).

It is a disadvantage of all previously known processes that a large amount of aluminum trichloride must be employed which must be led off with the effluent during working-up and pollutes the same. This also applies to the other Lewis acids iron chloride, titanium tetrachloride and tin tetrachloride mentioned in DE-A-3,531,837. It is therefore desirable to develop a process where the catalyst systems are easily worked up and can be recovered.

The present invention accordingly provides a process for the preparation of halogen-containing aromatic compounds of the formula

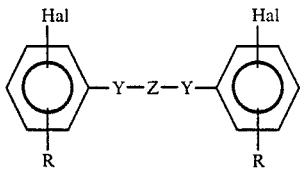

in which:
Hal denotes halogen,
R denotes H, $C_1$–$C_1$-alkyl, phenyl, halogen or trifluoromethyl,
Y denotes CO or $SO_2$ and
Z denotes an aromatic or heteroaromatic grouping, where
Y-Z-Y together also denote CO or $SO_2$, which comprises reacting a halomatic of the formula $RC_6H_4Hal$ (II) is reacted with a bis(acid halide) of the formula Hal-Y-Z-Y-Hal (III) in a molar ratio of at least 2:1 in the presence of hydrogen fluoride and boron trifluoride, in which in the formulae II and III Hal, R, Y and Z have the previously given meaning.

Preference is given to the preparation of compounds I which meet at least one of the features that Hal is fluorine or chlorine, R is hydrogen or halogen, Y is CO and Z is phenylene and, in particular, p-phenylene and that halogen is in a position other than the o-position to Y. Compounds having halogen in the p-position are very particularly preferred.

Possible aromatics of the formula II are, for example, fluorobenzene, o-, m- and p-difluorobenzene, o-m- and p-chlorofluorobenzene, o-, m- and p-bromofluorobenzene, o-, m- and p-fluoroiodobenzene, o-, m- and p-fluorotoluene, o- and p-fluorobiphenyl, o-, m- and p-trifluoromethyl-fluorobenzene, chlorobenzene, o-, m- and p-dichlorobenzene, o-, m- and p-bromochlorobenzene, o-, m- and p-chloroiodobenzene, 4-chlorobiphenyl, o-, m- and p-chlorotoluene, o-, m- and p-chlorotrifluoromethylbenzene, bromobenzene, o-, m- and p-dibromobenzene, o-, m- and p-bromoiodobenzene, o-, m- and p-bromotoluene, o-, m- and p-bromobiphenyl, o-, m- and p-bromobenzotrifluoride, iodobenzene, o- and p-diiodobenzene, o-, m- and p-iodotoluene and 3-iodotrifluoromethylbenzene. Bromobenzene is preferred and fluorobenzene and chlorobenzene are very particularly preferred. If R is different from hydrogen in the compounds $RC_6H_4Hal$, R is preferably halogen.

In the bis(acid halides) III Y is preferably CO. Z is, for example, the radical $C_6H_4$–E–$C_6H_4$ with E=O, $(CG_2)_m$, CO, S, SO or $SO_2$, where G is hydrogen, methyl, fluorine or trifluoromethyl and m is an integer from 0 to 4. If m is 0, the two phenylene radicals are thus bonded to one another by a single bond.

Examples of bis(acid halides) which may be mentioned are: phosgene, difluorophosgene, sulfuryl chloride, sulfuryl fluoride, terephthaloyl dichloride, isophthaloyl dichloride, 1,4- and 2,6-naphthalenedicarbonyl dichloride, 1,5-anthracenedicarbonyl dichloride, 4,4'-biphenyldicarbonyl dichloride,bis-(4,4'-chlorocarbonylphenyl)-methane,2,2-bis-(4,4'-chlorocarbonylphenyl)-propane, hexafluoro-2,2-bis-(4,4'-chlorocarbonylphenyl)-propane, di-(4,4'-chlorocarbonylphenyl) ketone, di-(4,4'-chlorocarbonylphenyl) ether, di-(4,4'-chlorocarbonylphenyl) sulfide, di-(4,4'-chlorocarbonylphenyl) sulfoxide, di-(,4,4'-chlorocarbonylphenyl) sulfone, pyridine-2,5-dicarbonyl dichloride, 2,5-thiophenedicarbonyl dichloride, 1,3- and 1,4-benzenedisulfonyl dichloride, 4,4'-biphenyldisulfonyl dichloride, 2,2-bis-(4,4'-chlorosulfonylphenyl)-propane, bexafluoro-2,2-bis-(4,4'-chlorosulfonylphenyl)-propane, di-(4,4'-chlorosulfonylphenyl) ether, di-0(4,4'-chlorosulfonylphenyl) sulfide, di-(4,4'-chlorosulfonylphenyl) sulfoxide, di-(4,4'-chlorosulfonylphenyl) sulfone and di-(4,4'-chlorosulfonylphenyl) ketone. Phosgene, sulfuryl chloride, terephthaloyl dichloride, di-(4,4'-chlorocarbonylphenyl) ketone, 4,4'-biphenyldicarbonyl dichloride, di-(4,4'-chlorocarbonylphenyl) ether, di-(4,4-chlorocarbonylphenyl) sulfide and di-(4,4'-chlorocarbonylphenyl) sulfone are preferred.

The compounds of the formula II and the formula III mentioned as examples are either known or can be prepared by analogous processes.

The end products obtained of the formula I are for example 4,4'-difluorobenzophenone, 4,4'-dichlorobenzophenone, bis-(4-fluorophenyl) sulfone, bis-(4-chlorophenyl)sulfone, 1,4-bis-(4-fluorobenzoyl)-benzene, 1,4-bis-(4-chlorobenzoyl)-benzene, 4,4'-bis-(4-fluorobenzoyl)-diphenyl ether, 4,4'-bis-(4-fluorobenzoyl)biphenyl, 4,4'-bis-(4-fluorobenzoyl)-diphenyl sulfide and 4,4'-bis-(4-fluorobenzoyl)-diphenyl sulfone.

2 to 10, preferably 2 to 3, moles of II are in general employed per mole of bis(acid halide) III in the process according to the invention. Furthermore, 0.1 or 1 to 100 moles, preferably 10 to 50 moles, and in particular 20 to 30 moles of hydrogen fluoride are in general employed per mole of bis(acid halide) III. Amounts of less than 1 mole of hydrogen fluoride are only used if starting from a bis(acid fluoride). In this case, the use of larger amounts of hydrogen fluoride is uncritical for the reaction. It is then advantageous to use only comparatively small amounts of hydrogen fluoride, usually not more than 30 and, in particular, 1 to 5 moles.

The process according to the invention is in generally carried out at temperatures from $-80°$ to $+200°$ C., preferably from $0°$ to $+50°$ C. The boron trifluoride is in general used in an amount of at least 2 moles per mole of bis(acid halide) III, for example from 2.5 to 10 moles. The process can be carried out at atmospheric pressure, but working at higher pressure, in particular at a total pressure of 5 to 70 bar, is preferred. If the process is carried out at elevated pressure, the process can, for example, be carried out in a stainless steel autoclave which is optionally lined with a resistant material such as polytetrafluoroethylene, the starting materials II and III being initially introduced and hydrogen fluoride being pumped in, for example in the molar amounts given above, based on the bis(acid halide) III.

It is often expedient to start from those bis(acid halides) in which Hal is fluorine. These compounds do not need to be employed as such, but in an advantageous embodiment are prepared in situ by reacting those compounds III in which Hal is chlorine, bromine or iodine with at least the equivalent amount of hydrogen fluoride. This transhalogenation may be carried out, for example, at $-20°$ to $+200°$ C., preferably at $40°$ to $80°$ C., in particular at $50°$ to $70°$ C., for example by keeping the mixture in intimate contact for 2 to 24 hours by stirring or shaking. The resulting hydrogen halide may be evaporated off, for example at $0°$ to $10°$ C., if desired via a column. Boron trifluoride is then introduced under pressure, usually at a temperature up to $50°$ C., and the crude product which still contains hydrogen fluoride is reacted under the abovementioned conditions.

In another embodiment, the compounds II and III may also be initially introduced in hydrogen fluoride. Boron trifluoride is then introduced under a pressure of 5 to 70 bar at the abovementioned temperatures and the reaction is carried out to give the compounds I.

Working-up is carried out by evaporating the boron trifluoride and the hydrogen fluoride. They may be reused. The crude product of the formula I obtained in this way may be purified by crystallization, if appropriate in the presence of a base such as MgO, Na$_2$CO$_3$ or K$_2$CO$_3$, washing or distillation or a combination of these measures.

The advantage of the process according to the invention is that the compounds II and III can be employed in equimolar amounts and the hydrogen fluoride and the boron trifluoride can be recovered without difficulty. There is thus no effluent in this process, nor are there any emissions of pollutants, which is of great importance for a modern process.

In addition, in contrast to the known process, which is carried out with aluminum chloride, a homogeneous reaction mixture is reacted according to the invention, so that no mixing or separation problems occur.

The bis-(4-halobenzoyl) compounds obtained by the process according to the invention, of which 1,4-bis-(4-fluorobenzoyl)-benzene and 1,4-bis-(4-chlorobenzoyl)-benzene are preferred, are useful monomers for chemically resistant plastics which are still resistant even at high temperatures. They may be used directly, without further purification, for polycondensations after dissolving in suitable solvents, if appropriate with the addition of solid bases, preferably Na$_2$CO$_3$, K$_2$CO$_3$ or MgO, and subsequent filtration if necessary, for example with hydroquinone to give polyether ketones.

The invention is illustrated by the examples below, where m.p. means melting point, h means hours and BFB means 1,4-bis-(4-fluorobenzoyl)-benzene.

EXAMPLES 1. 20.3 g of terephthaloyl dichloride, 19.2 g of fluorobenzene and 50 g of hydrogen fluoride were initially introduced into a 250 ml stainless steel autoclave and boron trifluoride was introduced under pressure at 10 bar. The autoclave was shaken for 16.5 h at room temperature. Working-up was carried out by initially evaporating the volatile components at room temperature and then at $60°$ to $100°$ C. and recrystallizing the residue from chlorobenzene in the presence of sodium carbonate. 19.76 g of 1,4-bis-(4-fluorobenzoyl)-benzene were obtained in the form of colorless crystals of m.p. $221°$ C. Examination by means of high pressure liquid chromatography (HPLC) gave a degree of purity of 99.5%.

2. As in Example 1, 20.3 g of terephthaloyl dichloride, 21.1 g of fluorobenzene and 50 g of hydrogenfluoride were reacted for 18 h at $50°$ C. at a BF$_3$ pressure of 11.5 bar. After working-up, 20 g of BFB were obtained (HPLC purity 99%).

3. The same batch as in Example 2 was reacted for 47 h at room temperature. 24.5 g of BFB were obtained (HPLC purity 99.5%).

4. 20.3 g of terephthaloyl dichloride, 21.1 g of fluorobenzene and 50 g of hydrogen fluoride were initially introduced at $0°$ to $10°$ C. into a 250 ml autoclave made of stainless steel and the mixture was shaken for 3 h at $50°$ C. It was then cooled to $0°$ C., the resulting HCl pressure was released and BF$_3$ was introduced at a pressure of 10 bar. The mixture was shaken for 15 h at room temperature and 25.6 g of BFB were obtained by working-up as in Example 1 (HPLC purity 99.5%).

5. Example 4 was repeated with the modification that the mixture was shaken for 16.5 h at room temperature at a BF$_3$ pressure of 64 bar. The yield of BFB was 28.8 g (HPLC purity 99.5%).

COMPARISON EXPERIMENT 1 (WITHOUT BF$_3$)

20.3 g of terephthaloyl dichloride, 21.1 g of fluorobenzene and 50 g of hydrogen fluoride were shaken for 24 h at room temperature in a 250 ml stainless steel autoclave. After working-up according to Example 1, no BFB was obtained.

COMPARISON EXPERIMENT 2 (WITHOUT HF)

20.3 g of terephthaloyl dichloride and 28.8 g of fluorobenzene were initially introduced into a 250 ml stainless steel autoclave, boron trifluoride was introduced at a pressure of 60 bar and the mixture was shaken for 26 h at room temperature. After working-up according to Example 1, 2.2 g of BFB were obtained.

6. 34 g (0.2 mol) of terephthaloyl difluoride, 115 g (1.2 mol) of fluorobenzene and 4 g (0.2 mol) of anhydrous hydrogen fluoride were initially introduced into a 250 ml stainless steel shaking autoclave. A total of 39 g (0.58 mol) of boron trifluoride was introduced under pressure and the mixture was shaken for 24 h at $20°$ to $40°$ C. The autoclave was depressurized and the reaction product was worked up as described in Example 1.54 g (83.8%) of BFB were obtained (HPLC purity 99%).

7. 17 g (0.1 mol) of terephthaloyl difluoride, 57.5 g (0.6 mol) of fluorobenzene and 5 g (0.25 mol) of anhydrous hydrogen fluoride were initially introduced into a 250 ml stainless steel shaking autoclave. The reaction was carried out in the same way as in Example 6 and 26.5 g (82.4%) of BFB (HPLC purity 99%) were obtained.

We claim:

1. A process for the preparation of halogen-containing aromatic compounds of the formula I

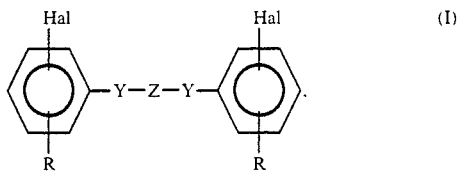

wherein
Hal represents halogen,
R represents H, $C_1$–$C_3$-alkyl, phenyl halogen or trifluoromethyl,
Y represents CO or $SO_2$ and
Z represents an aromatic or heteroaromatic group, and
Y-Z-Y together can also be CO or $SO_2$, which comprises reacting at a temperature in the range of from $-80°$ to $+200°$ C. a haloaromatic compound of the formula $RC_6H_4Hal$ (II) with a fluoride of a bisacid having the formula F-Y-Z-Y-F (III) in a molar ratio of at least 2:1 in the presence of hydrogen fluoride and of boron trifluoride, in formula II and III Hal, R, Y and Z having the aforementioned meaning, the hydrogen fluoride being applied in an amount of from 0.1 to 5 moles per mole of compound III and 2 to 10 moles of the compound II being reacted per mole of compound III.

2. A process as claimed in claim 1, wherein 2 to 3 moles of the compound II are reacted per mole of compound III.

3. A process as claimed in claim 1, wherein Z represents an aromatic group of the formula $C_6H_4$-E-$C_6H_4$ (IV) wherein E represents O, $(CG_2)_m$, CO, S, SO or $SO_2$, G represents hydrogen, methyl, fluorine or trifluoromethyl and m represents an integer of from 0 to 4.

4. A process as claimed in claim 1, wherein in formulae I and II Hal represents fluorine or chlorine.

5. A process as claimed in claim 1, wherein in formulae I and II R represents hydrogen or halogen.

6. A process as claimed in claim 1, wherein in formulae I and III Y represents CO.

7. A process as claimed in claim 1, wherein in formulae I and halogen is in a position other than the ortho-position to Y.

8. A process as claimed in claim 1, characterized by at least two of the features that in the compounds of the formulae I and II Hal represents fluorine or chlorine, R represents hydrogen or fluorine or chlorine, Y represents CO, Z represents phenylene and halogen is in a position other than the ortho-position to Y.

9. A process as claimed in claim 1, wherein compound II is fluoro-, chloro- or bromobenzene.

10. A process as claimed in claim 1, wherein a compound II is reacted to yield a compound in which the halogen is in p-position to Y.

11. A process as claimed in claim 1, wherein the hydrogen fluoride is applied in an amount of from 1 to 5 moles per mole of the fluoride of the bis-acid III.

12. A process as claimed in claim 1, wherein, the fluoride of the bisacid III is reacted as a crude product obtained by a reaction of a halide of a bis-acid III in which Hal represents chlorine, bromine or iodine, with at least an equivalent amount of hydrogen fluoride at a temperature in the range of from $-20°$ to $+200°$ C.

13. A process as claimed in claim 12, wherein the reaction has been carried out at a temperature in the range of from 40° to 80° C.

14. A process as claimed in claim 1, wherein the reaction is carried out at a pressure in the range of from 5 to 70 bar.

15. A process as claimed in claim 1, wherein the reaction is carried out at a temperature in the range of from 5° to 50° C.

16. A process as claimed in claim 1, wherein the boron trifluoride is applied in an amount of at least 2 moles per mole of the fluoride of the bis-acid III.

17. A process as claimed in claim 1, wherein the boron trifluoride is applied in an amount of from 2.5 to 10 moles per mole of the halide of the bis-acid III.

18. A process for the preparation of halogen-containing aromatic compounds of the formula I

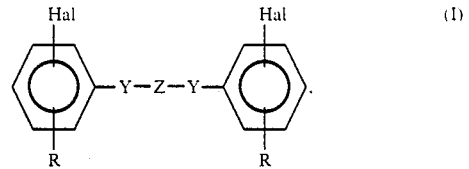

wherein
Hal represents halogen,
R represents H, $C_1$–$C_3$-alkyl, phenyl, halogen or trifluoromethyl,
Y represents CO or $SO_2$ and
Z represents a phenylene group, which comprises reacting at a temperature in the range of from $-80°$ to $+200°$ C. a haloaromatic compound of the formula $RC_6H_4Hal$ (II) with a fluoride of a bisacid having the formula F-Y-Z-Y-F (III) in a molar ratio of at least 2:1 in the presence of hydrogen fluoride and of boron trifluoride, in formulae II and III Hal, R, Y and Z having the aforementioned meaning, the hydrogen fluoride being applied in an amount of from 0.1 to 5 moles per mole of compound III and 2 to 10 moles of the compound II being reacted per mole of compound III.

19. A process as claimed in claim 18, wherein Z represents p-phenylene.

20. A process for the preparation of halogen-containing aromatic compounds of the formula I

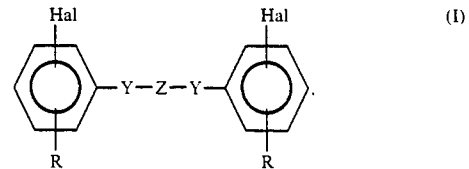

wherein
Hal represents chlorine or fluorine and is in the p-position to Y,

R represents H,
Y represents CO and
Z represents a phenylene group, which comprises reacting at a temperature in the range of from $-80°$ to $+200°$ C. a haloaromatic compound of the formula $RC_6H_4Hal$ (II) with a fluoride of a bisacid having the formula F-Y-Z-Y-F (III) in a molar ratio of at least 2:1 in the presence of hydrogen fluoride and of boron trifluoride, in formulae II and III Hal, R, Y, and Z having the aforementioned meaning, the hydrogen fluoride being applied in an amount of from 0.1 to 5 moles per mole of compound III, the boron trifluoride being applied in an amount of at least 2 moles per mole of the compound III, 2 to 3 moles of compound II being reacted per mole of compound III.

21. A process as claimed in claim 20, wherein Z represents p-phenylene.

22. A process as claimed in claim 20, wherein the hydrogen fluoride is applied in an amount of from 1 to 5 moles per mole of the fluoride of the bis-acid III.

23. A process as claimed in claim 20, wherein a fluoride III is used as crude product obtained by a reaction of a halide of a bis-acid III in which Hal represents chlorine, bromine or iodine, with at least an equivalent amount of hydrogen fluoride at a temperature in the range of from $-20°$ to 30 200° C.

24. A process as claimed in claim 20, wherein the reaction is carried out at a pressure in the range of from 5 to 70 bar.

25. A process as claimed in claim 20, wherein the reaction is carried out at a temperature in the range of from 5° to 50° C.

26. A process as claimed in claim 20, wherein the boron trifluoride is applied in an amount of from 2.5 to 10 moles per mole of the fluoride of the bis-acid III.

* * * * *

UNITED STATES PATENT AND TRADEMARK OFFICE
CERTIFICATE OF CORRECTION

PATENT NO. : 4,924,014
DATED : May 8, 1990
INVENTOR(S) : ANDREAS FUSS, ET AL.

It is certified that error appears in the above-identified patent and that said Letters Patent is hereby corrected as shown below:

In Column 1, line 52, "$C_1-C_1$-alkyl" should read

-- $C_1-C_3$-alkyl -- .

In Column 5, line 1, "Example 1.54 g" should read

-- Example 1.  54 g -- .

In Claim 1, column 5, line 35, "formula" should read --formulae--.

In Claim 7, column 5, line 56, please delete "and".

In Claim 16, column 6, line 20, "an .. amount" should read

-- an amount -- .

In Claim 17, column 6, line 24, "halide" should read --fluoride--.

UNITED STATES PATENT AND TRADEMARK OFFICE
CERTIFICATE OF CORRECTION

PATENT NO.   :   4,924,014
DATED        :   May 8, 1990
INVENTOR(S)  :   ANDREAS FUSS, ET AL.

It is certified that error appears in the above-identified patent and that said Letters Patent is hereby corrected as shown below:

In Claim 23, column 8, line 9, "30 200°" should read -- + 200°--.

Signed and Sealed this

Eleventh Day of June, 1991

Attest:

HARRY F. MANBECK, JR.

Attesting Officer

Commissioner of Patents and Trademarks